United States Patent [19]

Mueller et al.

[11] Patent Number: 5,342,979
[45] Date of Patent: Aug. 30, 1994

[54] PRODUCTION OF TERTIARY CARBOXYLIC ACIDS

[75] Inventors: Wolfgang H. E. Mueller; Manfred Hartmann, both of Marl, Fed. Rep. of Germany

[73] Assignee: Huels Aktiengesellschaft, Marl, Fed. Rep. of Germany

[21] Appl. No.: 32,555

[22] Filed: Mar. 17, 1993

Related U.S. Application Data

[63] Continuation of Ser. No. 648,700, Jan. 31, 1991, abandoned.

[30] Foreign Application Priority Data

Feb. 3, 1990 [DE] Fed. Rep. of Germany ....... 4003232

[51] Int. Cl.$^5$ ................................................ C11B 3/00
[52] U.S. Cl. ...................... 554/206; 554/175; 554/213; 562/517; 562/521; 252/DIG. 9
[58] Field of Search ............... 562/521, 517; 568/916; 554/208, 175, 213; 252/DIG. 9

[56] References Cited

U.S. PATENT DOCUMENTS 3,151,139  9/1964  van der Plas .............. 260/419
3,167,585  1/1965  Anderson et al. .......... 562/521
3,489,779  1/1970  Bearden, Jr. ............... 260/419
4,636,284  1/1987  English et al. ............. 568/916

FOREIGN PATENT DOCUMENTS 7323412  3/1969  Japan .
73/23412  7/1973  Japan .

OTHER PUBLICATIONS

Kusher et al, "Removal of Hydrocarbons From $C_{12-16}$ and $C_{10-18}$ Higher Fatty Acids", Chemical Abstracts, vol. 104, #12, 1986, p. 133, 90907u.
Wickson et al., "Now: NEO-Acids Go Commercial," Hydrocarbon Processing, vol. 43, No. 11, Nov. 1964, pp. 185–190, 1964.
Falbe (ed.), New Syntheses with Carbon Monoxide, Springer-Verlag, Berlin, 1980, pp. 406–408, 1980.
"Tert Nonanoic Acid Isolation–From Crude Product, Containing Isobutylene Tetramer" JP-AS 73/23412, Maruzen Oil Co., Ltd, 1969.
"Isolating Trimethlacetic Acid . . . " JP-AS 71/35724, Maruzen Oil Co. Ltd. 1968.
"Isolating Pivalic Acid–From Koch's Reaction Mixture Using Isobutylene Raw Material . . . " JP-AS 73/00807, Maruzen Oil Co., Ltd, 1968.

Primary Examiner—José G. Dees
Assistant Examiner—Deborah D. Carr
Attorney, Agent, or Firm—Millen, White, Zelano & Branigan

[57] ABSTRACT

In a process for the production of tertiary carboxylic acids, especially by "Koch synthesis", the byproducts, e.g., a dimer of tripropene, are removed from the reaction mixture by azeotropic rectification with alkanediols, e.g., 1,3-butanediol, as entrainers, thus obtaining the tertiary carboxylic acids in pure form.

21 Claims, 1 Drawing Sheet

PRODUCTION OF TERTIARY CARBOXYLIC ACIDS

This application is a continuation of application Ser. No. 07/648,700, filed Jan. 31, 1991, now abandoned.

BACKGROUND OF THE INVENTION

The invention relates to the production of tertiary carboxylic acids (also called neoacids) from carbon monoxide, the appropriate olefins, and water on an acid catalyst and, in particular, to the purification of the resultant products.

Tertiary carboxylic acids can be produced according to the so-called "Koch synthesis" from the appropriate olefins, carbon monoxide, and water. Thus, e.g., 2,2-dimethyl propanoic acid (trimethylacetic acid, pivalic acid) is obtained from isobutene:

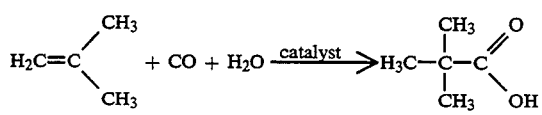

Mainly used as catalysts are strong protonic acids, such as, e.g., sulfuric acid, phosphoric acid, and hydrofluoric acid, or Lewis acids, such as, e.g., boron trifluoride, aluminum chloride, and antimony (V) chloride [Houben-Weyl, *Methoden der organischen Chemie* (Methods of Organic Chemistry), Fourth Edition, Vol. E5, 1985, p. 315).

In separating the byproducts resulting from the "Koch synthesis", it is known that prior to the distillation of the tertiary carboxylic acids, the reaction mixture can be washed with water (*Hydrocarbon Processing*, Vol. 43, No. 11, November 1964, pp. 186–187), as well as with sulfuric acid, sodium bicarbonate, and citric acid [*Ullmanns Encyklopaedie der technischen Chemie* (Ullmann's Encyclopedia of Industrial Chemistry), Fourth Edition, Vol. 9, p. 40, and J. Falbe, "New Synthesis with Carbon Monoxide, 1980, p. 407].

According to JP-AS 73/16897, the crude product containing the tertiary carboxylic acids is treated before distillation with an oxidizing agent, such as, e.g., air or oxygen, and, according to U.S. Department of Defense Publication No. 864,004, is catalytically hydrogenated.

DE-OS 15 68 391 teaches a process for the production of neoacids according to the "Koch synthesis", and the formed neoacids are obtained by extraction with cyclohexane and aqueous potassium hydroxide from the reaction product (see Example 2).

Also, according to U.S. Pat. Nos. 3,489,779 and 3,151,139, the formed neoacids are separated from the reaction mixture by extraction; namely, with heptane as the extraction agent or with an aqueous ammonia solution in the presence of a water-immiscible organic solvent which retains the impurities.

The processes according to the prior art for obtaining tertiary carboxylic acids from the crude product of the "Koch synthesis" are thus complex, expensive, and difficult to perform, especially in liquid-liquid extractions, where small amounts of secondary ingredients or impurities particularly hamper operations.

JP-AS 71/35724 discloses a process for obtaining trimethylacetic acid, in which dimeric and trimeric isobutene are distilled as azeotropic mixtures with water and n-amyl alcohol from the crude product obtained in the "Koch synthesis".

According to JP-AS 73/00807, the trimethylacetic acid crude product of the "Koch synthesis" is subjected to azeotropic distillation to remove as impurities dimeric isobutene with water as entrainer and trimeric isobutene with water and trimethylacetic acid as an entrainer. ("Entrainer" is synonymous with azeotropeformer and entraining agent.)

The working-up processes of JP-AS 71/35725 and JP-AS 73/00807 are suitable solely for the isolation of trimethylacetic acid, and only dimeric and trimeric isobutene can be azeotropically distilled off as impurities from the trimethylacetic acid crude product.

JP-AS 73/23412 discloses a process for obtaining tertiary nonanoic acids. In this case, tetrameric isobutene with diethylene glycol ether as the entrainer is separated by azeotropic distillation from the crude product obtained in the "Koch synthesis". This working-up process is suitable exclusively for isolating tertiary nonanoic acids, and basically only tetrameric isobutene can be separated from the impurities by distillation.

SUMMARY OF THE INVENTION

Therefore, an object of the invention is to develop a more economical and more easily workable process for the production of tertiary carboxylic acids, especially according to the "Koch synthesis", in which the formed tertiary carboxylic acids can be separated from the reaction mixture in a simple and effective way, in a form as free as possible from impurities.

Upon further study of the specification and appended claims, further objects and advantages of this invention will become apparent to those skilled in the art.

It was surprisingly found that the byproducts can be removed from the crude product of the "Koch synthesis" simply and in an economically attractive way by an azeotropic rectification with alkanediols as entraining agents, thereby obtaining the tertiary carboxylic acids in a purified form.

Therefore, to attain the objects of this invention, a process is provided for the production of tertiary carboxylic acids from carbon monoxide, wherein the appropriate olefins and water are reacted on an acid catalyst, which is characterized in that after the catalyst is removed, the other byproducts are removed from the reaction mixture by azeotropic rectification with alkanediols as entrainers, with the tertiary carboxylic acids being obtained as the bottoms fraction.

The production of the reaction mixture containing the tertiary carboxylic acids generally takes place according to the prior art "Koch synthesis".

The process according to the invention can most advantageously be used if the byproducts exhibiting boiling points similar to the produced tertiary carboxylic acids, e.g., within the boiling point range of the produced isomeric tertiary carboxylic acids, are removed from the reaction mixture by azeotropic rectification with alkanediols as entrainers, preferably after separation of the catalyst from the reaction mixture. (The separation of the catalyst is preferably conducted by washing with water.)

As is known, byproducts which boil in the same boiling range as the produced tertiary carboxylic acids cannot be separated from the latter by simple rectification.

A preferred variant of the process according to the invention is that before the azeotropic rectification with the alkanediols as entrainers, the unreacted olefinic starting materials are separated from the reaction mixture and, preferably, are recycled to the "Koch" reaction. This separation of the unreacted olefin is preferably conducted by simple rectification.

Preferably, the process according to the invention can be used for the production of tertiary carboxylic acids with 6 to 13 carbon atoms, especially for the production of tertiary nonanoic (neononanoic) acids and tertiary decanoic (neodecanoic) acids.

In the production of tertiary carboxylic acids according to the "Koch synthesis", the crude product contains considerable portions of byproducts. Byproducts are understood to be, e.g., olefins and paraffins produced from the starting materials and alcohols, esters, and carbonyl compounds formed by chemical reactions, as well as oligomerization and especially dimerization and trimerization products of the starting olefins. Other substances result by synthesis or decomposition of carbon chains of the olefins with secondary reactions. The process according to the invention is thus particularly suitable for removing such byproducts in the production of tertiary carboxylic acids.

In the azeotropic rectification of the invention, alkanediols are used which preferably form heteroazeotropes with the byproducts, i.e., with oligomers of the olefins and/or alcohols and/or esters and/or carbonyl compounds and/or paraffins and/or olefins. (A heteroazeotrope is an azeotrope which condenses into more than a single liquid phase.)

Conversely, also suitable as entraining agents are alkanediols which do not form heteroazeotropes but instead form homoazeotropes with the byproducts to be separated according to the invention, such as with, e.g., 2-methyl-2,4-pentanediol formed during the production of tertiary nonanoic and decanoic acids.

The azeotropic rectification used according to the invention with alkanediols as entrainers can be performed both batchwise and continuously.

Preferably, the azeotropic rectification with alkanediols as entrainers is performed at subatmospheric pressure, generally from about 4 to about 100 mbars.

For the production of tertiary nonanoic acids and/or tertiary decanoic acids, alkanediols with boiling points at 1 atmospheric pressure of less than 230° C. are preferably used as entraining agents, such as, e.g.:
1,2-propanediol;
1,2-butanediol;
1,3-butanediol;
1,4-butanediol;
2,3-butanediol;
1,2-pentanediol;
2,4-pentanediol;
1,2-hexanediol;
2,5-hexanediol; and
2,2-dimethyl-1,3-propanediol.

Particularly preferred is the use of 1,3-butanediol as the entrainer in the azeotropic rectification for the production of tertiary nonanoic acids and/or tertiary decanoic acids.

The following table illustrates the entraining capacity of 1,3-butanediol for various olefins at a pressure of 30 mbars.

| Azeotropic Points at P = 30 mbars (olefin = comp. 1; 1,3-butanediol = comp. 2) | | | |
|---|---|---|---|
| Olefin | $T_s$ (°C.) | $T_{az}$ (°C.) | $x_{az}$ |
| 1-tridecene | 122.2 | 107.8 | 0.433 |
| 1-tetradecene | 137.7 | 114.2 | 0.263 |
| dimeric tripropene | 158.6 | 118.1 | 0.055 |
| 1-hexadecene | 165.9 | 117.9 | 0.040 |

$T_s$ boiling point of pure olefin at P = 30 mbars
$T_{az}$ boiling point of the azeotrope at P = 30 mbars
$x_{az}$ molar portion of the olefin at the azeotropic point The composition and the boiling points of the azeotropes will, of course, vary depending on the pressure of the distillation.

Alkanediols with atmospheric boiling points of more than 230° C. which also form heteroazeotropes with the byproducts in the production of tertiary nonanoic acids and/or decanoic acids are also suitable for the separation of the byproducts from the reaction mixture.

The alkanediols preferably have 3–6 carbon atoms.

Novel azeotropic mixtures consist essentially of (a) $C_{18}$ hydrocarbons, particularly octadecene, especially 1-octadecene, and (b) 1,3-butanediol, 1,4-butanediol, or 1,5-pentanediol.

Following the azeotropic rectification using alkanediols as entrainers, the tertiary carboxylic acids are further purified, e.g., by simple distillation as opposed to azeotropic distillation.

The process according to the invention offers, in comparison to the processes according to the prior art, substantial advantages: less trouble-prone, high product purity, and the use of simple industrial equipment.

BRIEF DESCRIPTION OF THE DRAWING

The attached drawing is a schematic illustration of a preferred continuous process of the invention. It is described in detail in Example 17.

Without further elaboration, it is believed that one skilled in the art can, using the preceding description, utilize the present invention to is fullest extent. The following preferred specific embodiments are, therefore, to be construed as merely illustrative and not limitative of the remainder of the disclosure in any way whatsoever.

Figure 1:
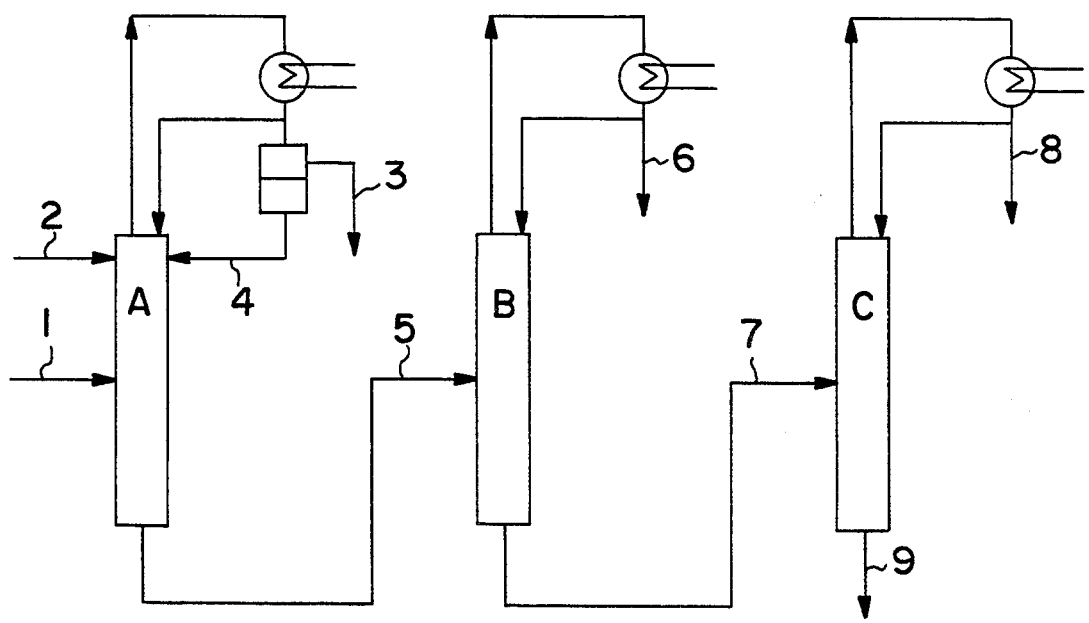

In the foregoing and in the following examples, all temperatures are set forth uncorrected in degrees Celsius; and, unless otherwise indicated, all parts and percentages are by weight.

The entire disclosures of all application, patents, and publications cited herein, and of corresponding Application No. P 40 03 232.9, filed Feb. 3, 1990, in the Federal Republic of Germany, are hereby incorporated by reference.

EXAMPLES

Example 1

2000 g of crude neodecanoic acid, freed of the catalyst and low-boiling components (such as, e.g., tripropene), is rectified batchwise with 2000 g of 1,3-butanediol as entrainer at a pressure at the column head of 4 mbars and a reflux ratio of 5, in a rectification column provided with a Sulzer laboratory packing 1 m long and a nominal width of 50 mm. The crude neodecanoic acid is produced in a known way according to the "Koch synthesis" from tripropene, carbon monoxide, and water with a combination of boron trifluoride, water, and copper(I) oxide as the catalyst at a pressure of 10 bars and a temperature of 30° C. According to gas chromatographic analysis, the following composition for the crude neodecanoic acid was determined:

76% by weight of decanoic acids;
23% by weight of $C_{18}$ hydrocarbons (a dimer of tripropene, i.e., a branched octadecene having an olefinic double bond); and
1% by weight of other substances.

In the rectification of the crude neodecanoic acid, the following fractions of the following compositions are removed partly under phase separation (as heteroazeotropes) at the following boiling points under a pressure of 4 mbars abs.:

Fraction 1 ($bp_4 \leq 85°$ C.) upper phase (156 g)

less than 0.1% by weight of 1,3-butanediol;
less than 0.1% by weight of decanoic acids;
83.3% by weight of C18 hydrocarbons; and
16.7% by weight of other substances, such as, e.g., other hydrocarbons, esters and carboxylic acids with less than 10 C atoms.

Fraction 1, lower phase (233 g)

87.7% by weight of 1,3-butanediol;
less than 0.1% by weight of decanoic acids;
0.3% by weight of $C_{18}$ hydrocarbons; and
12.0% by weight of other substances such as e.g., esters and carboxylic acids with less than 10 C atoms.

Fractions 2 to 5 ($bp_4 = 85°$ C.), upper phases (total 313 g)

less than 0.1% by weight of 1,3-butanediol;
less than 0.1% by weight of decanoic acids;
100.0% by weight of $C_{18}$ hydrocarbons; and
less than 0.1% by weight of other substances.

Fractions 2-5, lower phases (total 1293 g)

99.3% by weight of 1,3-butanediol;
0.5% by weight decanoic acids;
0.2% by weight of $C_{18}$ hydrocarbons; and
less than 0.1% by weight of other substances.

Starting with Fraction 6, a homogeneous distillate condensed:

Fractions 6-9 ($bp_4 = 86°-115°$ C.) (total 882 g)

Mixtures of 1,3-butanediol and decanoic acids.

Fractions 10-12 ($bp_4 = 115°-120°$ C.) (total 625 g)

More than 99.9% by weight of decanoic acids; 498 g of distillation residue:
84.8% by weight of decanoic acids; and
15.2% by weight of other substances (high boilers).

Example 2 Comparative Example

If the rectification of crude neodecanoic acid is performed as in Example 1, but without 1,3-butanediol as entrainer, there are obtained a maximum concentration of $C_{18}$ hydrocarbons of 38.0% by weight and a maximum concentration of decanoic acids of 98.3% by weight.

Example 3 Comparative Example

If Example 2 is repeated but with a reflux ratio increased from 5 to 25, a maximum concentration of $C_{18}$ hydrocarbons of 47.6% by weight and a maximum concentration of the decanoic acids of 98.6% by weight are achieved.

Example 4

Analogously to Example 1, the crude neodecanoic acid is rectified batchwise together with 1 000 g of 1,4-butanediol as entrainer. First, a mixture (1174 g) comes over at about 100° C., which separates into two liquid phases. The lighter phases (total 587 g) contain about 25% by weight of decanoic acids and about 71% by weight of $C_{18}$ hydrocarbons, as well as 0.5% by weight of 1,4-butanediol. The heavier phases (total 587 g) contain 65% by weight of 1,4-butanediol, 27% by weight of decanoic acids and 5% by weight of $C_{18}$ hydrocarbons besides small amounts of other substances, such as, e.g., other hydrocarbons. Then a binary azeotrope (1027 g) with 60% by weight of 1,4-butanediol and 40% by weight of decanoic acids and less than 0.4% by weight of $C_8$ hydrocarbons are removed at 101° to 106° C.; and, after an intermediate cut, a fraction (530 g) with a content of more than 99.9% by weight of decanoic acids comes over.

Example 5

Example 1 is repeated but with 1182 g of 1,2-propanediol instead of 2000 g of 1,3-butanediol as entrainer.

The lighter phases (total 415 g) of fractions coming over at about 71° C., which, after condensation, separate into two liquid phases, contain 99.8-99% by weight of $C_{18}$ hydrocarbons and 0.2-1.0% by weight of other substances, such as, e.g., other hydrocarbons. The heavier phases (total 4181 g) are composed of 99.8% by weight of 1,2-propanediol and 0.2% by weight of $C_{18}$ hydrocarbons. They are mostly fed back to the column as additional reflux. After an intermediate cut, 100.0% by weight of decanoic acid (1239 g) is removed at 119°-121° C.

Example 6

Example 1 is repeated but with 1118 g of 2,3-butanediol instead of 2000 g of 1,3-butanediol as entrainer.

The fractions coming over at 63° to 65° C. separate into two liquid phases. The lighter phases (total 385 g) contain 99.8% by weight of $C_{18}$ hydrocarbons and 0.2% by weight of 2,3-butanediol, the heavier phases (total 7484 g), which mostly are recycled to the column, contain 98.3% by weight of 2,3-butanediol, 1% by weight of $C_{18}$ hydrocarbons and 0.7% by weight of other substances, such as, e.g., carboxylic acids with less than 10 C atoms. After an intermediate cut, then decanoic acid (1178 g) with a content of more than 99.5% by weight and a content of less than 0.2% by weight of 2,3-butanediol and less than 0.3% by weight of $C_{18}$ hydrocarbons comes over at 119°-121° C.

Example 7

Example 1 is repeated but with 1063 g of 1,2-butanediol instead of 2000 g of 1,3-butanediol as entrainer.

The fraction coming over at 73°-75° C. separates into two liquid phases. The lighter phase (388 g) contains more than 99.5% by weight of $C_{18}$ hydrocarbons, less than 0.3% by weight of decanoic acids and less than 0.2% by weight of 1,2-butanediol. The related heavier phases are recycled to the rectification column. After an intermediate cut, fractions with a content of 99.5% to 100.0% by weight of decanoic acids (1250 g) are obtained.

Example 8

Example 1 is repeated but with 160 g of 1,5-pentanediol instead of 2000 g of 1,3-butanediol as entrainer. The rectification takes place at a pressure of 1 mbar abs.

The fractions first coming over at 87°–90° C. also separate here into two liquid phases. The lighter phases (total 601 g) contain 72% by weight of $C_{18}$ hydrocarbons besides 23% by weight of decanoic acids, less than 5% by weight of other substances, such as, e.g., carboxylic acids with less than 10 C atoms and less than 1% by weight of 1,5-pentanediol. The heavier phases are recycled to the column. Then, after an intermediate cut, a binary azeotrope (198 g) with 30% by weight of 1,5-pentanediol and 70% by weight of decanoic acids is removed; and, after an intermediate cut, decanoic acids (800 g) with a content of more than 99.5% by weight are obtained.

Example 9

Example 1 is repeated but with 550 g of 2,4-pentanediol instead of 2000 g of 1,3-butanediol as entrainer. The rectification takes place at a pressure of 1 mbar abs.

The fractions coming over at 57°–68° C. separate here into two liquid phases. The lighter phases (total 448 g) contain 99.8% by weight of $C_{18}$ hydrocarbons and 0.2% by weight 2,4-pentanediol. The heavier phases here also are recycled to the column. The decanoic acid fractions (total 1080 g), resulting after the intermediate cut, have the following composition: more than 99.5% by weight of decanoic acids, less than 0.3% by weight of $C_{18}$ hydrocarbons, and less than 0.2% by weight of 2,4-pentanediol.

Example 10

Example 1 is repeated but with 1667 g of 1,2-pentanediol instead of 2000 g of 1,3-butanediol as entrainer. The rectification takes place at a pressure of 1 mbar abs.

The fraction coming over at 68° C. separates also here into two liquid phases. The heavier phases are recycled to the column. The lighter phases (403 g) contains 99.6% by weight of $C_{18}$ hydrocarbons, 0.2% by weight of 1,2-pentanediol, and 0.2% by weight of other substances, such as, e.g., other hydrocarbons. The decanoic acid fractions (total 1246 g), resulting after the intermediate cut, have a content of more than 99.5% by weight.

Example 11

Example 1 is repeated but with 1000 g of crude neodecanoic acid and with 2800 g of methyl 2,4-pentanediol instead of 2000 g of 1,3-butanediol as entrainer. The rectification takes place at a pressure of 1 mbar abs.

The distillate (2913 g) with a boiling point of 63° C. does not separate into two liquid phases. It contains about 92% by weight of 2-methyl-2,4-pentanediol and 8% by weight of $C_{18}$ hydrocarbons. After an intermediate cut, a fraction (90 g) with about 80% by weight of decanoic acids and 20% by weight of 2-methyl-2,4-pentanediol comes over, and after a further intermediate cut, decanoic acids (433 g) with a content of more than 99.5% by weight are removed.

Example 12

Example 1 is repeated but with 895 g of 2,5-hexanediol instead of 2000 g of 1,3-butanediol as entrainer. The rectification takes place at a pressure of 1 mbar abs.

The fractions coming over at 76°–82° C. separate into two liquid phases. The heavier phases are recycled to the column. The lighter phases (total 371 g) contain 99.6% by weight of $C_{18}$ hydrocarbons, 0.2% by weight of 2,5-hexanediol, and 0.2% by weight of other substances, such as, e.g., carboxylic acids with less than 10 C atoms. After the intermediate cuts, fractions with 100.0% by weight of decanoic acids (846 g) are obtained.

Example 13

Example 1 is repeated but with 1102 g of 1,2-hexanediol instead of 2000 g of 1,3-butanediol as entrainer. The rectification takes place at a pressure of 1 mbar abs.

The fractions coming over at 75°–76° C. separate here, too, into two liquid phases. The lighter phases (total 446 g) contain 98.5% by weight of $C_{18}$ hydrocarbons, 1% by weight of 1,2-hexanediol and 0.5% by weight of other substances, such as, e.g., carboxylic acids with less than 10 C atoms. After several intermediate cuts, a 99.8% by weight decanoic acid (996 g) with a content of 0.2% by weight of $C_{18}$ hydrocarbons is obtained.

Example 14

Example 1 is repeated but with 743 g of 1,2-cyclohexanediol instead of 2000 g of 1,3-butanediol as entrainer. The rectification takes place at a pressure of 21 mbars abs.

The distillate does not separate into liquid phases. After separation of a fraction (214 g) with:
- 25% by weight of 1,2-cyclohexanediol,
- 2% by weight carboxylic acids with less than 10 C atoms,
- 58% by weight of hydrocarbons, and
- 15% by weight of other substances, fractions (total 620 g) with about 53% of 1,2-cyclohexanediol and about 47% by weight of $C_{18}$ hydrocarbons come over. After intermediate cuts with increasing amounts of decanoic acid, finally a fraction (851 g) with a content of more than 99.5% by weight of decanoic acid is obtained.

Example 15

Analogously to Example 1, 2000 g of crude neodecanoic acid, which, after separation of $C_8$ hydrocarbons, contains 80% by weight of nonanoic acid, 16% by weight of $C_{16}$ hydrocarbons, and 4% by weight of other substances, such as, e.g., other hydrocarbons, other carboxylic acids and esters, is rectified with 750 g of 1,3-butanediol as entrainer.

The crude neononanoic acid is produced in a known way according to the "Koch synthesis" from isooctene, carbon monoxide, and water with boron trifluoride, water, and copper(I) oxide as catalyst at a pressure of 10 bars and a temperature of 30° C.

The first fraction (356 g) coming over at 65°–76° C. and pressure of 4 mbars abs. separates into two liquid phases, and the lighter phase (231 g) is composed of 10% by weight of 1,3-butanediol, 52% by weight of $C_{16}$ hydrocarbons and 38% by weight of other substances, such as, e.g., other hydrocarbons. The other fractions, which are removed at 76° to 88° C., also separate into two liquid phases, whose lighter phases (total 195 g) contain 93% by weight of $C_{16}$ hydrocarbons, 6% by weight of other substances, such as, e.g., other hydrocarbons and esters and 1% by weight of 1,3-butanediol. The heavier phases are recycled to the rectification column. After several intermediate cuts, nonanoic acid (1153 g) with a purity of more than 99.9% by weight is removed.

Example 16

Example 15 is repeated but with 1174 g of 1,2-propanediol instead of 750 g of 1,3-butanediol as entrainer.

The first fraction coming over at 48°–65° C. and at a pressure of 5 mbars abs. separates into two liquid phases, and the lighter phase (123 g) is composed of 15% by weight of 1,2-propanediol, 15% by weight of $C_{16}$ hydrocarbons and 70% by weight of other substances, such as, e.g., other hydrocarbons. The other fractions, which are removed at 65°–75° C., also separate into two liquid phases, whose lighter phases (total 301 g) contain 96% by weight of $C_{16}$ hydrocarbons, 4% by weight of other substances, such as, e.g., esters and 0.3% by weight of 1,2-propanediol. After several intermediate cuts, nonanoic acid (1054 g) with 99.9% by weight purity is removed.

Example 17

1470 kg/h of crude neodecanoic acid, after separation of the catalyst and the unreacted nonene, is continuously rectified with 0.795 kg/h of 1,3-butanediol as entrainer in a system of three columns "A," "B," and "C."

In column "A" the byproducts are separated as azeotropic mixture with 1,3-butanediol and in column "B" the intermediate boilers are separated, while in column "C" neodecanoic acid is distilled by the top as pure product. The crude neodecanoic acid in a known way is produced according to the "Koch synthesis" from tripropene, carbon monoxide and water with boron trifluoride, water and copper(I) oxide as catalyst at a pressure of 10 bars and a temperature of 30° C.

DETAILED DESCRIPTION OF THE DRAWING

The attached drawing is a flow sheet of the system comprising the three columns "A," "B," and "C."

The related process parameters of all three columns are tabulated in Table 1.

The streams, referring to the reference figure in the drawing, have the following throughputs:

| | |
|---|---|
| stream 1 (crude neodecanoic acid) | 100 parts by weight/hour |
| stream 2 | 0.03 parts by weight/hour |
| stream 3 | 18.6 parts by weight/hour |
| stream 4 | 62.8 parts by weight/hour |
| stream 5 | 81.4 parts by weight/hour |
| stream 6 | 0.4 parts by weight/hour |
| stream 7 | 81.0 parts by weight/hour |
| stream 8 | 71.2 parts by weight/hour |
| stream 9 | 9.8 parts by weight/hour |

Table 2 shows the chemical composition of the individual streams in % by weight, which was determined by gas chromatographic analysis. As can be seen in Table 2, the azeotropic mixture, removed by the head in column "A," separates into two liquid phases (streams) 3 and 4, and the byproducts are almost completely removed with the lighter phase 3. The heavier phase 4, mainly containing the entrainer 1,3-butanediol, is recycled to column "A."

Small amounts of intermediate boilers, mainly carboxylic acids with a carbon number less than 10, are separated in column "B."

If a small amount of these lower carboxylic acids in the pure neodecanoic acid is tolerated and no greater demands are made on the color index, column "B" can be eliminated.

In column "C," the neodecanoic acid as overhead product (stream 8) is obtained with a purity of 99.89% by weight and with an outstanding color index (APHA: 5–10).

TABLE 1

| | Process parameters | | |
|---|---|---|---|
| | Column "A" | Column "B" | Column "C" |
| Column packings | 30 actual plates | 6 m braided metal packing | 5 m braided metal packing |
| Product feed | 10th plate from bottom | 4 m height from bottom | 1 m height from bottom |
| Entrainer feed | column head | — | — |
| Column head pressure | 10 mbars | 30 mbars | 10 mbars |
| Column head temperature | 93° C. | 142° C. | 134° C. |
| Column bottom temperature | 168° C. | 169° C. | 166° C. |
| Reflux ratio | 1 | 50 | 4 |

TABLE 2

| Stream | Composition in wt. % of individual streams referred to in the drawing | | | | | | | | |
|---|---|---|---|---|---|---|---|---|---|
| | 1 | 2 | 3 | 4 | 5 | 6 | 7 | 8 | 9 |
| 1,3-Butanediol | — | 100 | 0.2 | 81.4 | — | — | — | — | — |
| $C_9$ hydrocarbons | 0.1 | — | 0.4 | — | — | — | — | — | — |
| Intermediate cut | 0.8 | — | 4.0 | 9.5 | — | 5.9 | — | — | — |
| Carboxylic acids with C number less than 10 | 0.4 | — | 1.7 | 7.4 | 0.1 | 32.4 | — | — | — |
| Neodecanoic acids | 78.5 | — | 1.1 | 0.2 | 96.2 | 61.7 | 96.3 | 99.89 | 70.1 |
| Intermediate cut | 1.6 | — | 6.2 | 0.2 | 0.6 | — | 0.6 | — | 5.0 |
| $C_{18}$ hydrocarbons | 13.3 | — | 71.0 | 1.1 | 0.1 | — | 0.1 | 0.11 | — |
| Tailings | 5.3 | — | 15.5 | 0.2 | 3.0 | — | 3.0 | — | 24.9 |

The intermediate cuts in Table 2 refer to peaks in the gas chromatogram. Thus, the first mentioned intermediate cut refers to peaks between the group of nine hydrocarbon peaks and the group of peaks for carboxylic acids of less than 10 C atoms, predominantly 9 C atoms. It is assumed that different secondary alcohols and esters are present in the first intermediate cut. The second intermediate cut refers to peaks occurring after the peaks for neodecanoic acid and before the peaks for the $C_{18}$ hydrocarbons. In the second cut would be, for example, acids with more than 10 C atoms and hydrocarbons, as well as esters with less than 18 C atoms.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process conducted in a reaction zone for the production of tertiary carboxylic acids from carbon monoxide, at least one olefin, and water in contact with an acid catalyst, the improvement which comprises removing byproducts comprising oligomers of the starting material olefin(s) and/or alcohols and/or esters and/or carbonyl compounds and/or paraffins and/or other olefins from the resultant reaction mixture by azeotropic rectification with an alkanediol as an entrainer.

2. A process according to claim 1, wherein the azeotropic rectification is conducted after the separation of the catalyst.

3. A process according to claim 1, wherein the byproducts exhibit boiling points within the boiling point range of the produced isomeric tertiary carboxylic acid.

4. A process according to claim 1, wherein unreacted starting olefin is separated from the crude reaction mixture before said azeotropic rectification.

5. A process according to claim 4, wherein the unreacted olefin is recycled to the reaction zone.

6. A process according to claim 1, wherein the tertiary carboxylic acids have 6–13 C atoms.

7. A process according to claim 6, wherein the tertiary carboxylic acids have 9–10 C atoms.

8. A process according to claim 1, wherein byproducts are removed in the form heteroazeotropes.

9. A process according to claim 7, wherein an alkanediol with an atmospheric boiling point under standard pressure of less than 230° C. is used as the entrainer for the production of at least one (a) tertiary nonanoic acid and (b) tertiary decanoic acid in the azeotropic rectification.

10. A process according to claim 9, wherein 1,3-butanediol is used as the entrainer.

11. A process according to claim 1, wherein the azeotropic rectification is conducted under a subatmospheric pressure of 4–100 mbars.

12. A process according to claim 10, wherein the azeotropic rectification is conducted under a subatmospheric pressure of 4–100 mbars.

13. A process according to claim 10, wherein tertiary decanoic acids are produced, and the byproducts comprise a dimer of tripropene.

14. A process according to claim 1, wherein the alkane diol is a 1,2-propanediol; 1,2-butanediol; 1,3-butanediol; 1,4-butanediol; 2,3-butanediol; 1,2-pentanediol; 2,4-pentanediol; 1,2-hexanediol; 2,5-hexanediol; or 2,2-dimethyl-1,3-propanediol.

15. A process according to claim 1, wherein 1,3-butanediol is used as the entrainer.

16. A process according to claim 1, wherein said crude neodecanoic acid contains not more than 1% by weight of water.

17. In a process conducted in a reaction zone for the production of neodecanoic acid from carbon monoxide, tripropene, water, boron trifluoride and a catalyst, the improvement which comprises purifying the neodecanoic acid by a process comprising:

(a) subjecting crude neodecanoic acid to azeotrophic distillation in a first distillation zone with 1,3-butanediol, to remove byproducts in the form of a heteroazeotropic overhead, condensing resultant overhead heteroazeotrope to form two phases, a lighter phase and a heavier phase wherein byproducts are concentrated in said lighter phase, and recycling the heavier phase to the first distillation zone as reflux;

(b) removing a semi-purified neodecanoic acid from the bottom of said first distillation, passing resultant semipurified neodecanoic acid to a second distillation zone to remove, as overhead, carboxylic acids having a carbon number less than 10; and (c) removing further purified neodecanoic acid from said second distillation zone; and passing said further purified neodecanoic acid to a third distillation zone to remove neodecanoic acid as an over head product stream.

18. A process according to claim 17, wherein said resultant crude reaction mixture contains not more than 1% by weight of water.

19. An azeotropic composition consisting essentially of (a) a $C_{18}$ hydrocarbon and (b) 1,3-butanediol, 1,4-butanediol, or 1,5-pentanediol.

20. An azeotropic composition according to claim 19, wherein the $C_{18}$ hydrocarbon is a dimer of tripropene.

21. An azeotropic composition according to claim 19, wherein (b) is 1,3-butanediol.

* * * * *